United States Patent [19]

Larson et al.

[11] Patent Number: 5,040,527
[45] Date of Patent: Aug. 20, 1991

[54] METERED DOSE INHALATION UNIT WITH SLIDE MEANS

[75] Inventors: Douglas A. Larson, River Forest; Thomas J. Danowki, Schaumburg, both of Ill.

[73] Assignee: Healthscan Products Inc., Cedar Grove, N.J.

[21] Appl. No.: 629,386

[22] Filed: Dec. 18, 1990

[51] Int. Cl.⁵ ............................................. A61M 11/00
[52] U.S. Cl. .............................. 128/200.23; 128/200.14
[58] Field of Search ..................... 128/200.14, 203.28, 128/200.23, 200.18, 203.15, 203.12, 207.14

[56] References Cited

U.S. PATENT DOCUMENTS

| | | |
|---|---|---|
| 3,456,646 | 7/1969 | Phillips . |
| 3,592,357 | 7/1971 | Welch . |
| 3,789,843 | 2/1974 | Armstrong . |
| 3,809,294 | 5/1974 | Torgeson . |
| 3,897,779 | 8/1975 | Hansen . |
| 3,994,421 | 11/1976 | Hansen . |
| 4,292,966 | 10/1981 | Mono . |
| 4,484,577 | 11/1984 | Sackner . |
| 4,534,343 | 8/1985 | Nowacki et al. ............... 128/203.15 |
| 4,592,348 | 6/1986 | Waters . |
| 4,706,663 | 11/1987 | Makiej . |
| 4,796,614 | 1/1989 | Nowaeki . |
| 4,852,561 | 8/1989 | Sperry . |

*Primary Examiner*—Edgar S. Burr
*Assistant Examiner*—Lisa E. Malvaso
*Attorney, Agent, or Firm*—Schweitzer, Corman & Gross

[57] ABSTRACT

An apparatus for dispensing a measured amount of a spray-entrapped product, typically dispensed by a metered dose inhaler device, includes an elongated passageway having a mouthpiece portion and a main chamber portion. The metered dose inhaler is mounted between the mouthpiece and main chamber portions such that upon operation its spray is directed away from the mouthpiece. A two-position valve is provided to allow a first, low-level flow to be developed through the unit, followed by a higher flow rate as the metered dose inhaler unit is operated. This increased flow, passing through the device in the direction opposite to that of the MDI spray, contacts the spray plume to cause a high level of mixing and a decrease in spray particle size which results in an efficient draw of the spray medication into the lungs of the user.

11 Claims, 3 Drawing Sheets

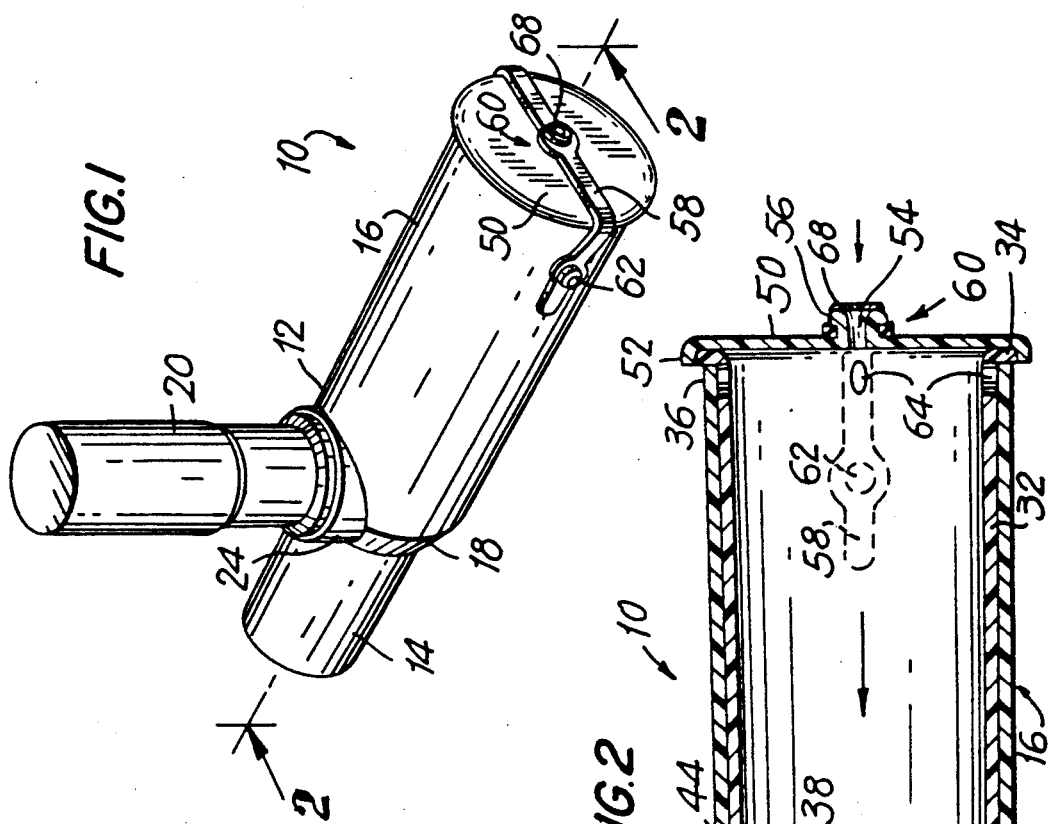
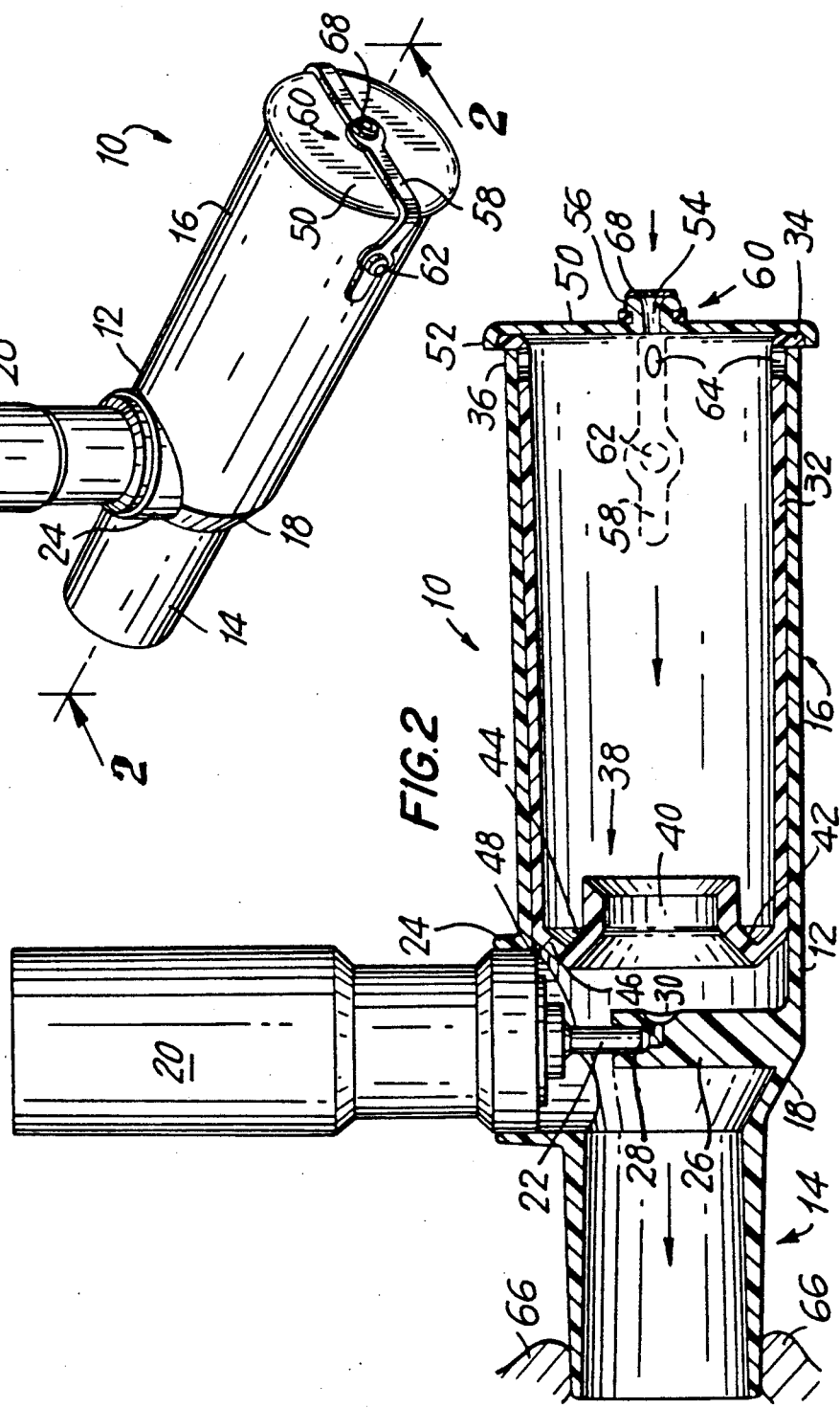

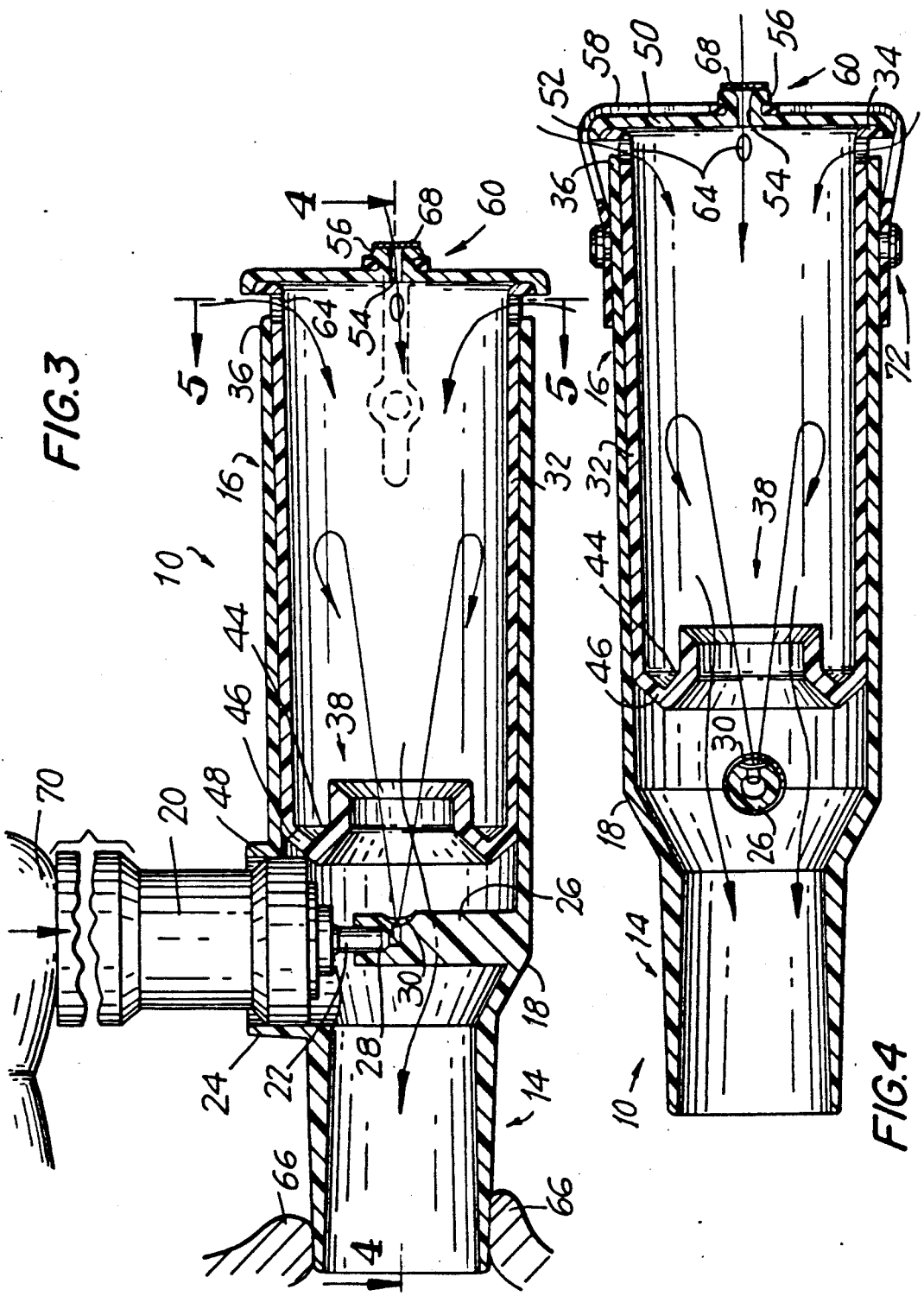

METERED DOSE INHALATION UNIT WITH SLIDE MEANS

BACKGROUND OF THE INVENTION

Many ailments and conditions of the human body require the administration of medication into the lungs of the patient. Typically, medication is provided by way of a metered dose inhalation (MDI) apparatus, comprising a pressurized container of the medication with appropriate valving to dispense a fixed amount of medication upon activation of the valve unit. The medication is inhaled to deliver the dispensed dose to the lungs.

While the amount of medication released per MDI cycle is accurately metered, the amount of medication actually reaching the lungs is far from consistent. To direct the medication to the lungs, the user must create an inspiratory flow of air, and must further time the flow to capture and engage the flow of medication, normally in the form of a mist, as it is released by the MDI. In addition, the high velocity of the emitted spray often results in a large portion of the drug being deposited in the mouth and oropharyngeal area, causing an unpleasant aftertaste, drug loss, and on occasion candidiasis.

To assist the user, a variety of devices have been developed to channel the MDI output. These devices, called "spacers", typically create a residence volume to accept the atomized spray until a breath is taken. Often, however, these devices introduce additional problems and complications, including awkwardness of use and the creation of complicated mechanisms which can defeat the inherent simplicity of the MDI system. The devices also often fail to gain user acceptance, as they are not small enough to provide the chronic respiratory disease patient with the ability to use the unit inconspicuously.

BRIEF DESCRIPTION OF THE INVENTION

The present invention provides a MDI spacer unit which couples the actuation of the unit with inhalation. The medication spray is directed away from the mouth and teeth, and contacts and mixes with an oppositely directed flow of inspiratory air. As a result of this mixing, the length of the medication plume is reduced, allowing the patient to inhale the plume in a full breath. Accordingly, the proper dose of medication can be effectively administered within a unit that has a relatively small resident volume. This allows a compact unit to be produced.

Reversal of the medication spray causes the spray droplets to be diffused and evaporated. Remaining large drops will have the tendency to settle into the spacer chamber, rather than being drawn into the mouth of the user and being deposited on the mouth and teeth. Thus, a greater volume of medication capable of reaching the lungs is delivered to the user.

These and other benefits are achieved in the present invention by providing an elongated chamber divided into a mouthpiece section and a main chamber section. A transverse aperture adapted to accept the valve-bearing end of a metered dose inhalation dispenser unit is provided between the mouthpiece and main chamber portion. Nozzle means direct the MDI spray into the main chamber in a direction away from the mouthpiece when the metered dose inhalation dispenser is operated. The open end of the main chamber portion of the unit is provided with first and second air-inlet aperture means, the first aperture being continuously open while the second aperture means has cover means coupled to the MDI dispenser whereby upon operation of the dispenser to release a dose of the medication, the cover means is displaced from a first position closing the aperture means to a second position whereby the aperture means are opened.

In operation, the patient inspires through the mouthpiece of the unit, the first aperture means allowing only a relatively small flow of air through the unit and into the mouth and lungs. Upon operation of the MDI dispenser, causing a metered dose of medication to enter the main chamber, the cover means is simultaneously opened, allowing a relatively large volume inrush of air to travel through the chamber in the direction opposite to that of the medication, as a result of the suction applied by the user. This rush impinges upon the MDI medication plume, reversing the plume's direction, and carrying it into the lungs of the user. Releasing the MDI dispenser to return to its normal closed position closes the cover means, resealing the second aperture means and resetting the apparatus for a subsequent dispensation. During periods of non-use, the MDI dispenser may be stored within the main chamber, providing a compact unit.

DESCRIPTION OF THE DRAWINGS

A fuller understanding of the present invention and the features and benefits thereof will be achieved upon consideration of the following detailed description of a preferred, but nonetheless illustrative, embodiment of the invention when reviewed in conjunction with the annexed drawings, wherein:

FIG. 1 is a perspective view of the unit with an MDI dispenser mounted thereon;

FIG. 2 is a side elevation view, in section, along line 2—2 of FIG. 1;

FIG. 3 is a side elevation view, in section, along line 2—2, detailing operation as medication is injected into the main chamber;

FIG. 4 is a top plan view, in section, along line 4—4 of FIG. 3;

DETAILED DESCRIPTION OF A PREFERRED EMBODIMENT

Figure 6:
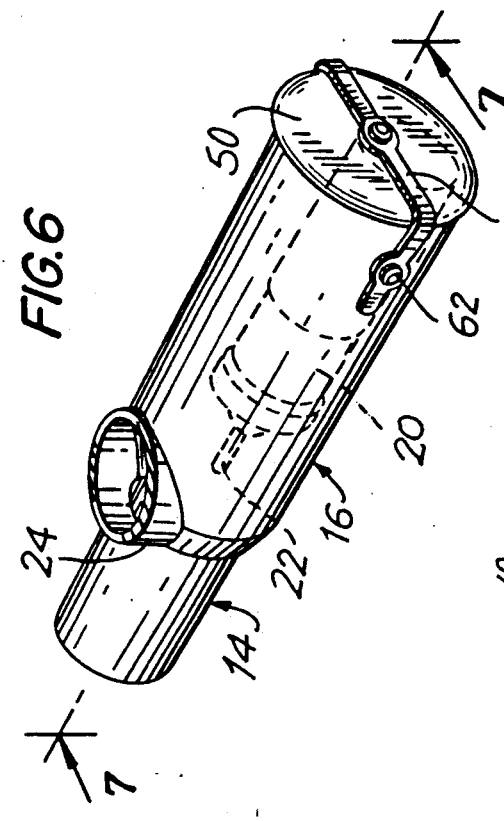
FIG. 6 is a perspective view illustrating, in phantom, storage of the MDI dispenser within the spacer body.

Referring to FIGS. 1 and 2, spacer unit 10 comprises an elongated, generally tubular member 12 forming a mouthpiece section 14 and a main chamber portion 16, connected by an intermediate portion 18 which supports metered dose inhaler dispenser 20.

As known in the art, the MDI dispenser 20 includes a nozzle 22 projecting from an end of the unit. Depression of the nozzle with respect to the body of the MDI unit causes a measured and metered dose of the contained medication to exit, in the form of a spray, through the nozzle. To accommodate the dispenser 20, the intermediate portion 18 of the spacer unit is provided with a circular bore in the chamber wall surrounded by peripheral upstanding lip 24. The lip 24 may be of varying height about its circumference, due to the difference in diameter between main chamber portion 16 and mouthpiece portion 14. In a preferred embodiment, the inner diameter of the main chamber portion may be on the order of 1.2 inches with the mouthpiece inner diameter being approximately 0.74 inches, with a small outward flare along its length.

An internal pedestal 26, located directly below the MDI-accepting aperture, extends upwardly within intermediate portion 18, and is provided with a right angle bore 28, the vertical portion of which is dimensioned to accept and support the MDI nozzle 22. The lower end of the vertical portion may include a seat portion beveled at a 45 degree angle to accept various diameter MDI valve stems. The horizontal portion of the bore terminates in a flared portion 30, causing the MDI medication to be sprayed into the main chamber portion 16 in a direction away from the mouthpiece 14. It is to be appreciated that downward pressure applied to the MDI dispenser with the spacer unit 10 held rigidly will depress the nozzle 22 with respect to the dispenser, activating the dispenser spray.

Positioned within the main chamber portion 16 is tubular slide element 32, whose exterior diameter is chosen to interfit with the internal diameter of the main chamber portion. Slide unit 32 is of elongated configuration, having a lipped first end 34 which serves as a stop against the distal end 36 of main chamber portion 16, and an integral nozzle 38 at its second end.

In particular, nozzle portion 38 comprises a reduced diameter central passageway portion 40, whose center line is aligned with the horizontal portion of right angle bore 28, and which is joined to proximal end 42 of slide unit 32 by intermediate angular transition portion 44, which creates a tapered entrance into passageway 40. The angular transition portion 44 includes inwardly-angled wall 46, against which the lower edge 48 of the MDI dispenser rests. The angle between the wall 46 and the horizontally-extending portion of the slide is preferably about 135 degrees. With the slide fully inserted into main chamber portion 16, wall 46 just clears lower edge 48 with the MDI nozzle fully inserted into the bore 28. The passageway 40 maintains the velocity of the inspiratory air flow to insure reversal of the spray plume from the dispenser 20 before it transverses the full length of the slide element. The passageway diameter is preferably 0.50 inches.

The distal, lipped end 34 of slide unit 32 is covered by a cap or cover 50 of generally circular configuration having a peripheral lip 52 which overlies the lipped end portion 34. A bore 54 extends centrally through the cover, and may preferably be surrounded by a collar 56. The bore provides a first air-inlet aperture means into the slide unit and main chamber portion 16. An elastic band 58 may be affixed about the reduced diameter neck 60 of the collar, the ends of the band being attached to approximately-dimensioned projections 62 on the exterior of main chamber portion 16 to removably retain the cover against the end of the slide unit. The band, installed in a tensioned state, further biases the slide and cover into the position depicted in FIG. 2, providing a restoring force against rightward motion of the slide, which occurs due to the force exerted against angled wall 46 by the edge 48 of the dispenser 20 as the dispenser is depressed.

A series of apertures 64 are located and spaced about the periphery of the slide unit 32 proximate the capped end thereof, and are so positioned to be normally overlaid and covered by the distal end of main chamber portion 36, but exposed as the slide unit moves rightwardly with respect to the main chamber portion. These apertures provide a second air-inlet aperture means into the slide and main chamber portion 16 and, in conjunction with the first air inlet aperture means 54, form a variable sized air inlet means for the main chamber. In a preferred form, the apertures 64 are 4 in number and are in the form of 0.031 by 0.222 inch slots. The aperture 54 in cap 50 is 0.062 inch in diameter.

Operation of the unit is as follows: With the MDI dispenser in place, the user embraces the mouthpiece 14 with his or her lips 66, and inhales through the unit. In the start position of FIG. 2, the apertures 64 on the slide 32 are overlaid by the distal end of the main chamber 16, and accordingly a relatively low volume airflow is developed through the unit by ambient air entering the chamber solely through cap bore 54. A flapper or other form of noise generator 68 may be incorporated into collar 56 to provide an oral indication that a proper airflow rate has been developed.

Figure 5:
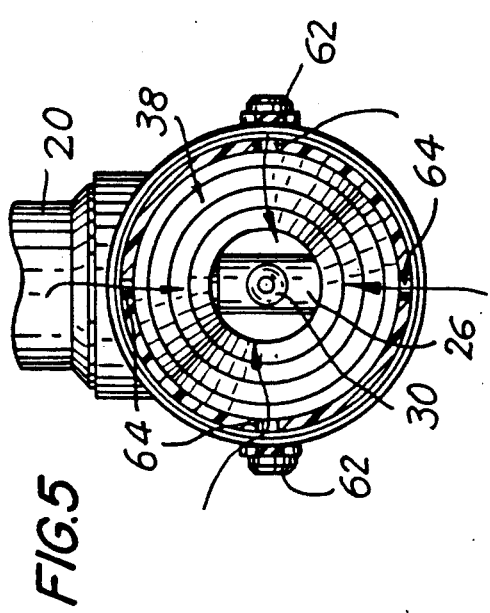
FIG. 5 is an end elevation view, in section, taken along line 5—5 of FIG. 3.

When the airflow is developed, and as the user continues to inhale, the MDI dispenser 20 is depressed, as depicted in FIGS. 3 through 5. As shown therein, depression by the user's hand 70 upon the upper portion of the dispenser against the properly supported spacer unit 10 drives the dispenser body downward through the aperture formed by wall 24 with respect to the nozzle 22, causing the internal valve of the MDI dispenser to open and dispensing the medication spray through the nozzle. The spray is directed into main chamber portion 16 by the directional bore 28.

The downward pressure upon the MDI dispenser also causes its lower edge 48 to further bear against the angled wall 46, driving it and slide unit 32 rightwardly, overcoming the retaining force of the elastic band 58. This relative travel with respect to the main chamber portion 16 positions the second apertures 64 beyond the distal end of the main chamber portion, exposing them to the ambient air and allowing an increased flow of air to enter the main chamber to be drawn into the mouth and lungs of the user. In a preferred embodiment, the apertures 64 are opened prior to the time the medication is released. This relationship may be adjusted by varying the cam action relationship between the angled wall 46 and the lower edge of the MDI dispenser.

As a low-level airflow was previously created through the cap bore 54, the opening of the additional apertures 64 causes a higher flow rate of air to enter and travel through the unit, into which the simultaneously-emitted medication plume is released. This draws the medication back through the unit and into the mouth and lungs of the user. The meeting of the counter-directed flows improves dispersion by mixing the spray with to-be inspired ambient air, reduces the size of the spray droplets by increasing evaporation of the liquid in the droplets and assists in the removal of remaining large droplets from the stream such that the airflow entering the mouth will not deposit the carried medication on the mouth surfaces, but rather allows the medication to reach the lungs of the user. The size of apertures 64 maintains the flow rate of inspiration to approximately 30 liters/minutes at inspiratory vacuum pressure of 10 cm of water. In order to double the flow rate, the inspiratory vacuum would have to be quadrupled.

Because of the small internal volume of the spacer, all the suspended medication will be inhaled into the lungs within approximately ¼ second after the spray from the MDI dispenser ceases. It is thus not necessary for the MDI dispenser to be held in the depressed position for the duration of the inspiratory breath, but only for the time period necessary to release the measured dose of medication. Release of the downward pressure on the MDI dispenser causes the slide unit to return to the left, rest position as shown in FIG. 2 by the restoring force of the elastic band 58. The angled wall 46 may further provide a secondary drive to raise the MDI dispenser. The second apertures 64 are closed, returning airflow through the unit to the initial, low volume state.

Figure 7:
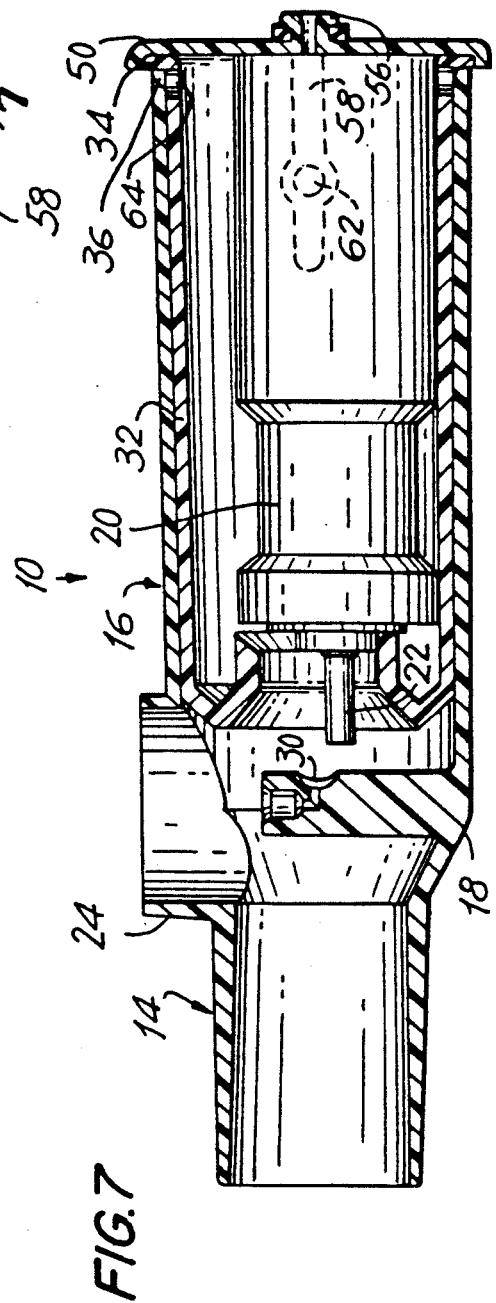
FIG. 7 is a side elevation view, in section, taken along line 7—7 of FIG. 6 showing the positioning of the dispenser within the spacer body.

As may be appreciated in connection with consideration of FIGS. 6 and 7, the spacer unit of the present invention may further provide for a convenient storage mechanism for the MDI dispenser 20. In particular, the diameter of the main chamber 16 and slide 32 are such as to allow the dispenser 20 to be placed within the slide by removal of the cap 50 which exposes the open end of the slide. With the MDI dispenser placed within the chamber, the cap may be replaced and retained by the band 58, thus providing a secure location for the dispenser and further insuring that the dispenser and spacer remain together for subsequent use. The projections 62 on the exterior of main chamber portion 16 may be formed with a reduced diameter neck 72 to facilitate connection and removal of the band therefrom.

It will be apparent to one skilled in the art that variations in the details of the embodiments specifically illustrated and described may be made without departing from the true spirit and scope of the invention as defined in the claims.

We claim:

1. Apparatus for dispensing a measured amount of a spray-entrapped produce for introduction into the lungs of a user, comprising an elongated passageway having a mouthpiece portion terminating at a first end and a main chamber portion terminating at a second end, said mouthpiece and main chamber portions being joined by an intermediate section, said intermediate section comprising means for supporting a metered does inhalation dispenser having a body and an extending nozzle, said intermediate section having means for directing the metered output of said dispenser into said main chamber portion and in a direction away from said first end; first and second air inlet aperture means for the introduction of ambient air into said main chamber portion for inhalation by the user, said first and second aperture means located at said second end; and valve means operatively coupled to said metered does inhalation unit for activation by movement of said metered does inhalation unit and to said second air inlet apertures, said valve means having a first position wherein said second inlet air apertures are closed and a second position wherein said second air inlet apertures are opened as said metered does inhalation dispenser is moved and activated to output into said main chamber portion.

2. The apparatus of claim 1, wherein said valve means comprises a sleeve mounted and slidable within said main chamber.

3. The apparatus of claim 2, wherein said sleeve comprises a tubular member having a first end comprising a reduced diameter passageway proximate the metered dose inhalation dispenser and a second end comprising said valve means proximate said main chamber portion second end.

4. The apparatus of claim 2, wherein said first aperture means are located in a removable cap mounted to said sleeve.

5. The apparatus of claim 4, wherein said valve is biased into said first position.

6. The apparatus of claim 4, wherein said first position is maintained by an elastic band operatively mounted between said sleeve and said main chamber portion.

7. The apparatus of claim 6, wherein said band is operatively connected to said sleeve by mounting to said cap.

8. The apparatus of claim 5, wherein said valve is operatingly coupled to said metered dose inhalation unit and said second air inlet apertures whereby said second air inlet apertures are opened prior to the time said inhalation dispenser is activated to output.

9. The apparatus of claim 5, wherein said second air inlets are adapted to restrict air flow rate to about 30 liters/minute at an inspiratory vacuum pressure of 10 cm of water.

10. The apparatus of claim 3, wherein said tubular member is of a length and diameter sufficient to receive the metered dose inhalation dispenser therein for storage purposes.

11. An apparatus for dispensing a measured amount of a spray-entrapped product for introduction into the lungs of a user, comprising an elongated, hollow passageway having a first mouthpiece end and an opposed second end; a pedestal located within said passageway adapted to receive the nozzle of a metered dose inhaler and having means to direct the spray output thereof within said passageway towards said second end; a variable air inlet means located at said second end adapted to provide a first low-flow rate of inspiratory air through said passageway at a first operative position and second higher flow rate of inspiratory air through said passageway at a second operative position; and means for repositioning said air inlet means from said first to said second position upon the commencement of the release of the spray output of the metered dose inhaler by movement of said metered dose inhaler whereby an increased inspiratory flow is created with the release of the spray whereby the spray is contacted by said flow to cause the inhalation of the spray by the user.

* * * * *